US009109260B1

(12) United States Patent
French et al.

(10) Patent No.: US 9,109,260 B1
(45) Date of Patent: Aug. 18, 2015

(54) IDENTIFICATION OF BACTERIA BY AMPLIFICATION AND PROBING

(75) Inventors: Gary Lawrence French, Kent (GB); Richard Michael Anthony, Kent (GB); Timothy James Brown, London (GB)

(73) Assignees: King's College London, London (GB); The Guy's & St. Thomas' National Health Trust Guy's Hospital, London (GB)

( * ) Notice: Subject to any disclaimer, the term of this patent is extended or adjusted under 35 U.S.C. 154(b) by 0 days.

(21) Appl. No.: 09/914,176

(22) PCT Filed: Mar. 1, 2000

(86) PCT No.: PCT/GB00/00740

§ 371 (c)(1),
(2), (4) Date: Jun. 6, 2005

(87) PCT Pub. No.: WO00/52203

PCT Pub. Date: Sep. 8, 2000

(30) Foreign Application Priority Data

Mar. 2, 1999 (GB) .................................. 9904804.3

(51) Int. Cl.
*C12Q 1/68* (2006.01)
(52) U.S. Cl.
CPC .......... *C12Q 1/689* (2013.01); *C12Q 2531/113* (2013.01); *C12Q 2531/143* (2013.01); *C12Q 2565/50* (2013.01)

(58) Field of Classification Search
None
See application file for complete search history.

(56) References Cited

U.S. PATENT DOCUMENTS

| 5,292,874 | A | 3/1994 | Milliman |
| 5,521,300 | A | 5/1996 | Shah et al. |
| 5,582,974 | A | 12/1996 | Nietuspki et al. |
| 5,582,978 | A | 12/1996 | Shah |
| 5,683,876 | A | 11/1997 | Hogan |
| 5,703,217 | A | 12/1997 | Mabilat et al. |
| 5,958,679 | A | 9/1999 | Hogan et al. |
| 5,994,066 | A * | 11/1999 | Bergeron et al. ................. 435/6 |
| 6,001,564 | A | 12/1999 | Bergeron et al. |
| 6,384,208 | B1 | 5/2002 | Edwards et al. |
| 6,605,709 | B1 | 8/2003 | Breton |

FOREIGN PATENT DOCUMENTS

| EP | 0 395 292 A | 10/1990 |
| WO | WO 88 03957 A | 6/1988 |
| WO | WO-88/09397 A1 | 12/1988 |
| WO | WO 90 14444 A | 11/1990 |
| WO | WO-95/03412 | 2/1995 |
| WO | WO 96 00298 A | 1/1996 |
| WO | WO 96 24686 A | 8/1996 |
| WO | WO-00/36146 | 6/2000 |
| WO | WO-2004/029299 | 4/2004 |
| WO | WO-2004/106547 | 12/2004 |
| WO | WO-2008135931 A2 | 11/2008 |

OTHER PUBLICATIONS

Blattner et al. (1997) The complete genome of *Escherichia coli* K-12. Science. vol. 277, pp. 1453-1462.*
GenBank Accession No. U00096. (1997) p. 1616. Accessed Dec. 15, 2005.*
Van Camp et al. Amplification and Sequencing of Variable Regions in Bacterial 23S Ribosomal RNA Genes with Conserved Primer Sequences. Current Microbiology (1993) 27: 147-151.*
McCabe et al. Bacterial species identification after DNA amplification with a universal primer pair. Molecular Genetics and Metabolism (1999) 66: 205-211.*
Gurtler et al. New approaches to typing and identification of bacteria using the 16s-23s rDNA spacer region. Microbiology (1996) 142: 3-16.*
Brosius et al. Complete nucleotide sequence of a 23S ribosomal RNA gene from *Escherichia coli*. Proceedings of the National Academy of Sciences, USA (1980) 18(7): 201-204.*
Kawasaki et al. Genetic Analysis Using Polymerase Chain Reaction-Amplified DNA and Immobilized Oligonucleotide Probes: Reverse Dot-Blot Typing. Methods in Enzymology (1993) 218: 369-381).*
Lowe et al. A computer program for selection of oligonucleotide primers for polymerase chain reactions. Nucleic Acids Research (1990) 18(7): 1757-1761.*
Paster et al. Identification of oral *Streptococci* using PCR-based, reverse-capture, checkerboard hybridization. Methods in Cell Science (1998) 20: 223-231.*
GenBank Accession No. X68425 for *S. aureus* 23S rRNA, Mar. 29, 1993 [online], [retrieved on Sep. 19, 2012], retrieved from the Internet: <URL: //www.ncbi.nlm.nih.gov/nuccore/x68425>.*
GenBank Accession No. X87284.1 for *K. pneumoniae* 23S rRNA, Jul. 3, 1997 [online], [retrieved on Nov. 7, 2013], retrieved from the Internet: <URL: //www.ncbi.nlm.nih.gov/nuccore/x87284.1>.*

(Continued)

*Primary Examiner* — Angela M Bertagna
(74) *Attorney, Agent, or Firm* — Foley & Hoag LLP (57) ABSTRACT

A method for identifying bacteria in a sample is described which comprises amplifying a portion of the 23S rDNA present in the sample using, as one primer, a degenerate primer set comprising one or more DNA molecules consisting essentially of DNA having the sequence(s) 5'GCGATTTCYGAAYGGGGRAACCC (SEQ ID NO: 1), the other primer consisting of DNA having the sequence 5'TTCGCCTTTCCCTCACGGTACT (SEQ ID NO: 2) and testing the resulting amplicon by hybridization to one or more oligonucleotide probes designed to identify one or more bacteria likely to be present in the sample. The method allows for the identification of at least 8 and considerably more bacterial species in a single test, including *Escherichia coli*, *Staphylococcus aureus*, *Pseudomonas aeruginosa*, *Enterococeus* spp., *Klebsiella* spp., *Enterobacter* spp., *Proteus* spp., *Pneumococci*, and coagulase-negative *Staphylococci*. One or more novel oligonucleotides for use in this test are immobilized on a solid carrier and incorporated in a diagnostic test kit for use in hospitals and other environments.

5 Claims, 1 Drawing Sheet

(56) References Cited

OTHER PUBLICATIONS

Lew, A. E., and Desmarchelier, P.M., "Detection of *Pseudomonas pseudomallei* by PCR and hybridization," *Journal of Clinical Microbiology*, vol. 32, No. 5, 1994, pp. 1326-1332.

Ludwig, W., et al., "PCR-based preparation of 23S rRNA-targeted group-specific polynucleotide probes," *Applied and Environmental Microbiology*, vol. 60., No. 9, 1994, pp. 3236-3244.

Inacio, J., et al., "Efficient Identification of Clinically Relevant *Candida* Yeast Species by Use of an Assay Combining Panfungal Loop-Mediated Isothermal DNA Amplification with Hybridization to Species-Specific Oligonucleotide Probes," J. of Clin. Microbiol. 46(2):713-720 (Feb. 2008).

Ludwig, et al., "Complete 23S Ribosomal RNA Sequences of Gram-positive Bacteria with a Low DNA G+C Content," System Appl. Microbiol. 15(4):487-501 (1992).

He, Zhili, et al. "Empirical Establishment of Oligonucleotide Probe Design Criteria," Applied and Environmental Microbiology, 71(7): 3753-3760 (Jul. 2005).

Mulle, Jennifer G., et al. "Empirical Evaluation of Oligonucleotide Probe Selection for DNA Microarrays," PLoS One; 5(3): e9921 (Mar. 2010).

* cited by examiner

IDENTIFICATION OF BACTERIA BY AMPLIFICATION AND PROBING

FIELD OF THE INVENTION

This invention relates to the identification of bacteria and more particularly, although not exclusively, to the identification of clinically important bacteria in biological samples e.g. blood. The invention is of special application to the identification of clinically important bacteria isolated in a hospital laboratory and obtained directly from clinical specimens, including positive blood culture bottles and fresh blood specimens. For convenience, the invention will be described primarily in the context of clinical needs but it will be appreciated that it has wide application outside this field.

BACKGROUND OF THE INVENTION

Eight bacterial species account for 65% of all blood culture isolates, although this varies with patient population. Typically these are *Escherichia coli* (~20%), *Staphylococcus aureus* (~20%), *Pseudomonas aeruginosa* (7%), *Enterococcus* spp. (5%), *Klebsiella* spp. (~5%), *Enterobacter* spp. (~4%), *Proteus* spp, and *Pneumococci* (~3%). In addition coagulase negative *Staphylococci* are frequently isolated from patients with intra-vascular devices but many of these isolates are clinically insignificant. The remaining 35% of blood culture isolates comprise upwards of 50 different species. Rapid detection of these numerous species with a single test would be very useful.

In recent years much effort has been invested in the production of species specific primers which can be used to identify an organism in a simple PCR reaction. If a PCR product of the expected size is produced with a set of these primers the presence of the target bacterium can be predicted with almost total certainty. Unfortunately this approach is not ideal for analyzing samples which may contain one of many pathogens. Analysis of such specimens using this approach requires a multiplex PCR containing a complex mixture of primers, a series of individual PCR reactions run in parallel to detect each species which may be present, or a series of PCR reactions run sequentially. Because of the potentially large number of different bacterial species that may be isolated from blood, these methods are unsatisfactory for the routine screening of general microbiological specimens.

SUMMARY OF THE INVENTION

A better approach is to use a single pair of primers to amplify DNA from a variety of organisms and then to analyze the sequence of the resulting product to determine from which species it originated. Primers directed at conserved stretches of DNA will produce an amplicon e.g. a PCR product from almost all species of bacteria. The region usually chosen is the 16S rDNA or the 16S 23S rDNA spacer region. The 16S 23S rDNA spacer region is highly variable within many species, frequently containing tRNA genes, and the length and sequence of amplified products can be used to type strains within a single species. In contrast the 16s rDNA is highly conserved and, as a large amount of sequence data is available on public computer databases, sequence data can give a definitive identification of the species of a bacterium in many cases. Unfortunately some species of clinical significance have identical or very similar 16s rDNA sequences which would be impossible or difficult to discriminate using this region alone.

We have now found that by targeting the large ribosomal sub-unit (23s rDNA) with novel specially designed oligonucleotide primers, specified hereinafter, and amplifying a portion of this DNA we can identify a large number of bacteria by means of a single test or at most a very small number of tests. For convenience, amplification by means of the polymerase chain reaction (PCR) will be referred to throughout the following description. It will be appreciated, however, that any other amplification technique can alternatively be used e.g. transcription mediated amplification (TMA), reverse transcriptase polymerase chain reaction (RTPCR), Q-beta replicase amplification, and single strand displacement amplification. Some modification of the primers used for PCR may be necessary when using these alternative methods. In the case of the TMA method, such modification will usually require the addition of promoter and recognition sequences to the primers of the present invention.

In accordance with the present invention the bacterial species are detected by amplifying bacterial 23S rDNA, and identified by using the amplified product (amplicon) to probe one or more oligonucleotides in a reverse hybridization system. After amplification by universal primers, the sequence of the amplicon has to be determined. Direct sequencing is complex and expensive. Sequence variation can be identified by restriction digests, but this is not a practical way to detect a wide range of variants. According to this invention the labelled amplicon is preferably hybridized to a panel or an array of oligonucleotides immobilized on a solid phase such as, for example, nylon membranes or synthesized in situ on silicon wafers. Since both the target and the probe are present at much higher concentrations than is typical for a Southern blot these hybridization reactions can be carried out in very short periods of time (less than 1 hour). This method is referred to as reverse hybridization. Reverse hybridization allows a very large series of sequence variations to be positively identified and lends itself to automation.

DETAILED DESCRIPTION OF INVENTION

The present invention comprises primers that amplify a portion of the 23S rDNA. The DNA sequences of these primers are set out below.

| Sequence 5' to 3' | |
|---|---|
| Forward primer ST23SP6 | |
| SEQ ID No 1 | GCGATTTCYGAAYGGGGRAACCC |
| Reverse Primer ST23SP10 | |
| SEQ ID No 2 | TTCGCCTTTCCCTCACGGTACT |

The sequences of the primers and oligonucleotides are given herein and expressed in standard IUB/IUPAC nucleic acid code. The primers, especially the reverse primer, are appropriately labelled e.g with Digoxigenin (as in the Example given below), biotin, or fluorescein. Any other labelling system can be used. Hybridization can also be detected by using the oligonucleotides to construct molecular beacons.

The Forward primer sequence given above contains the symbols Y and R. In accordance with standard terminology for use with degenerate sequences, Y represents nucleotides C or T and R represents nucleotides A or G. The symbols Y and R are used to indicate variability of base permutations at "wobble" regions in the sequence. The Forward primer reagent is therefore prepared as a degenerate primer set using a mixture of the appropriate nucleotides for incorporation at the wobble points.

The PCR products produced by these primers, from a range of medically important Gram positive and Gram negative bacterial cultures, are characterized by hybridization to an array of oligonucleotides designed to identify taxonomic groups. Using this procedure, which takes typically less than four hours, we have been able to identify a wide range of genera and species. This approach allows bacteria and mixtures of bacteria to be identified by molecular methods without the need for a priori knowledge of the causative agent or agents.

In summary, the present invention comprises a method for identifying bacteria in a test sample which comprises amplifying a portion of the 23S rDNA present in the sample using a primer pair comprising one primer consisting essentially of one or more oligonucleotides having the sequence or sequences
5'GCGATTTCYGAAYGGGGRAACCC (SEQ ID NO: 1) and a second primer consisting essentially of an oligonucleotide having the sequence
5'TTCGCCTTTCCCTCACGGTACT (SEQ ID NO: 2).
and testing the resulting amplicon by probing a set of oligonucleotides designed to identify bacteria which may be present in the sample by hybridising to their respective amplicon. In a set of oligonucleotides suitable for use with this method, the oligonucleotides are designed to hybridise to the products of the amplification reaction in a single test and therefore under a single set of hybridisation conditions.

According to the present invention, the sets of oligonucleotides which may be used hybridise in parallel to a range of amplicons under the same hybridisation conditions and can therefore be used in a single test for the identification of a range of different organisms.

The oligonucleotide probes, the sequences of which are set out below, can be used singly for the identification of certain individual species or in a panel or array for the identification of many different species. There is theoretically no limit to the number of oligonucleotide targets employed and the number of species that can be identified. Ideally the oligonucleotides used should each hybridize only to one bacterial species and to all members of that species. Thus with an ideal array, a unique profile consisting of species specific spots would be seen, giving identification to the species level. In practice, two or more oligonucleotide spots may be required for many species and in some cases several such spots may allow identification of variation within a species. In addition, some identifications can be made by comparing the relative intensities of hybridization of individual species to individual oligonucleotides. The assessment of hybridization can be quantified by visual or automated methods.

For example, 27 oligonucleotides have been used for the unambiguous identification of *Pseudomonas aeruginosa, Proteus mirabilis, Enterococcus feacium* and *Enterococcus feacalis*, as well as *Staphylococcus aureus*, coagulase negative *Staphylococcus, Listeria* species, *Stenotrophomonas maltophilia, Burkholderia cepacia*, and *Escherichia coli*. Usually, therefore, it will be desirable to provide oligonucleotides to probe not only for the 8, 10, or more of the microorganisms commonly occurring in hospital samples or the samples being tested in other situations, but also for other organisms likely to be encountered. Preferably, probes for at least 30 different species of micro-organism will be present on the support substrate used in the test.

The detection of short sequences in amplified DNA is a straightforward procedure that can be carried out on a massively parallel scale. This may be achieved by hybridizing a labelled PCR product to an array of oligonucleotides immobilized on a solid support e.g. a membrane, glass slides, or microtitre trays, or synthesized in situ on silicon wafers.

This assay can be easily extended to identify a wider range of bacterial species with the addition of oligonucleotides without increasing the complexity of performing the assay.

The oligonucleotides are:

| Oligo | Primary Target organism | Sequence 5' to 3' |
|---|---|---|
| 1a | *Proteus mirabilis* | SEQ ID No 3 AATAGCAGTGTCAGGAGAACGGTCT |
| 1b | *Proteus mirabilis* | SEQ ID No 4 ATAGCCCCGTATCTGAAGATGCT |
| 1c | *Escherichia coli* | SEQ ID No 5 CCAGAGCCTGAATCAGTGTGT |
| 2a | *Klebsiella oxytoca* | SEQ ID No 6 TCCCGTACACTAAAACGCACAGG |
| 2b | *Klebsiella pneumoniae* | SEQ ID No 7 TCCCGTACACCAAAATGCACAGG |
| 2c | *Escherichia coli* | SEQ ID No 8 CAGAGCCTGAATCAGTATGTG |
| 3a | *Enterobacter cloacae* | SEQ ID No 9 TCCCGTACACGAAAATGCACAGG |
| 3b | *Esh. coli, Citrobacter* spp. | SEQ ID No 10 CCCGTACACAAAAATGCACA |
| 3c | *Salmonella enterica* | SEQ ID No 11 AGAGCCTGAATCAGCATGTGT |
| 4a | *Streptococcus* spp. A | SEQ ID No 12 AGAAGAATGATTTGGGAAGATC |
| 4b | *Pseudomonas aeruginosa* | SEQ ID No 13 GCTTCATTGATTTTAGCGGAAC |
| 4c | *Haemophilus influenzae* | SEQ ID No 14 GTGAGGAGAATGTGTTGGGAAG |
| 5a | *Streptococcus* spp. B | SEQ ID No 15 AGAAGAAGACCTTGGGAAAGG |
| 5b | *Enterococcus faecalis* | SEQ ID No 16 GGTAGTCTGTTAGTATAGTTGAAG |
| 5c | *Aeromonas hydrophilia* | SEQ ID No 17 TGGAACGGTCCTGGAAAGGC |
| 6a | *Streptococcus* spp. B | SEQ ID No 18 AGAAGAACTACCTGGAAGGT |
| 6b | *Enterococcus faecium* | SEQ ID No 19 GGTAGTTCTTTCAGATAGTCGG |
| 6c | *Staphylococcus warneri* | SEQ ID No 20 ACGGAGTTACAAAAGTATATATTAGTTTTT |
| 7a | *Staphylococcus aureus* | SEQ ID No 21 ACGGAGTTACAAAGGACGACATTA |
| 7b | *Staphylococcus* spp.(+*Listeria* spp.) | SEQ ID No 22 GGTTGTAGGACACTCTATACGGAGTT |
| 7c | *Staphylococcus saprophticus* | SEQ ID No 23 ACGGAGTTACAAAAGAACAGACTAGTTTTT |
| 8a | *Staphylococcus epidermidis* | SEQ ID No 24 ACGGAGTTACAAAAGAACATGTTAG |
| 8b | *Staphylococcus carnosus* | SEQ ID No 25 ATGGAGTTACAAAAGAATCGATTAG |
| 8c | *Staphylococcus haemolyticus* | SEQ ID No 26 ACGGAGTTACAAAGGAATATATTAGTTTTT |
| 9a | *Burkholderia cepacia* | SEQ ID No 27 CGTATTGTTAGCCGAACGCTCT |
| 9b | *Stenotrophomonas maltophilia* | SEQ ID No 28 AGCCCTGTATCTGAAAGGGCCA |
| 9c | *Listeria* spp. | SEQ ID No 29 ACGGAG'TTACAAAAGAAAGTTATAATTTT |
| 10a | *Streptococcus oralis* | SEQ ID No 12 AGAAGAATGATTTGGGAAGATC |
| 10b | *Streptococcus anginosus* | SEQ ID No 15 AGAAGAAGACCTTGGGAAAGG |
| 10c | *Streptococcus thermophilus* | SEQ ID No 30 AGAAGAACTACCTGGGAAGGT |
| Oligonucleotides for use in an extended array. | | |
| 31 | *Streptococcus* spp. | SEQ ID No 31 ACGGCAGAAGGGCAAACCGAATTTTT |
| 32 | *Streptococcus* spp. | SEQ ID No 32 GGCAGGAGGGCAAACCGAAGATTTTTT |

| Oligo | Primary Target organism | Sequence 5' to 3' |
|---|---|---|
| 33 | Streptococcus spp. | SEQ ID No 33 GGCAAGAGGGCAAACCGAAGATTTTT |
| 34 | Acinetobacter spp. | SEQ ID No 34 CGCTCTGGGAAGTGCGAACGTTTT |
| 35 | Escherichia coli | SEQ ID No 35 GAAAGGCGCGCGATACAGGGTTTT |
| 36 | Enterobacter cloacae | SEQ ID No 36 GAAAGTCCGACGGTACAGGGTTTT |
| 37 | CNS A | SEQ ID No 37 ACGGAGTTACAAAAGAACATGTTAGTTTTT |
| 38 | CNS B | SEQ ID No 38 ACGGAGTTACAAAAGAATITGTTAGTTTTT |
| 39 | Plesiomonas shigelloides | SEQ ID No 39 GTTAGTGGAACGGATTGGAA |
| 40 | Neisseria gonorrhoeae | SEQ ID No 40 TGACCATAGCGGGTGACAGTCTTT |
| 41 | Neisseria meningitidis | SEQ ID No 41 TGACCATAGTGGGTGACAGTCTTT |
| 42 | Campylobacter spp. | SEQ ID No 42 GTGAGTTTAGCAGAACATFCTG |
| 43 | Campylobacter lari | SEQ ID No 43 TAAGTAAGGTTAGTAGAACACTCT |
| 44 | Helicobacter pylori | SEQ ID No 44 CATCCAAGAGAACGCTITAGCA |
| 45 | Ralstonia spp. | SEQ ID No 45 AATGGGATCAGCCTTGTACTCT |
| 46 | Esh. coli 3 | SEQ ID No 46 TCTGGAAAGGCGCGCGATACA |
| 47 | Enterobacter 1 | SEQ ID No 47 GTCTGGAAAGTCCGACGGTAC |
| 48 | Chlamydia pneumoniae | SEQ ID No 48 ACCATATTTTTAATATGGGGTTTTT |
| 49 | Chlamydia psittaci | SEQ ID No 49 CCACATTTTTAATGTGGGG |
| 50 | Chlamydia trachomatis | SEQ ID No 50 CCGAGCTGAAGAAGCGAGGGTTT |
| 51 | Coxiella burnetti | SEQ ID No 51 CCTTTCGAGGTTATGTATACTGAA |
| 52 | Rhodococcus erythropolis | SEQ ID No 52 GGTGTTGCATTCGTGGGGTTG |
| 53 | Rhodococcus fascians | SEQ ID No 53 GGGTTGCGTATGGAGGGTTG |
| 54 | Mycobacterium tuberculosis | SEQ ID No 54 GCGCTACCCGGCTGAGAGG |
| 55 | Mycobacterium avium | SEQ ID No 55 CTACCTGGCTGAGGGGTAGTC |
| 56 | Mycobacterium kansasii | SEQ ID No 56 GGACGACGTCTCAGCTCTA |
| 57 | +ve Positive control | SEQ ID No 57 TGACTGACCGATAGYGAACCAGTA |
| (40) | Neisseria gonorrhoeae | SEQ ID No 58 TGACCATAGCGGGTGACAGTC |
| (41) | Neisseria meningitidis | SEQ ID No 59 TGACCATAGTGGGTGACAGTC |
| (48) | Chlamydia pneumoniae | SEQ ID No 60 ACCATATTTTTAATATGGGG |
| (50) | Chlamydia trachomatis | SEQ ID No 61 CCGAGCTGAAGAAGCGAGGG |

The sequences of the primers and oligonucleotide priobes are also given hereinafter as Sequence Listings in written form and supplied in computer readable form. The information recorded in computer readable form is identical to the written sequence listing.

EXEMPLIFICATIONS

Methodology

The methods we have used are described as follows:
Bacterial Strains.

The stored strains used are listed in Table 1. Organisms were stored in glycerol broth at −70° C.
Blood Cultures.

Blood cultures may be performed by using an enrichment technique e.g. the Vital® automated system (Bio Merioux, France). In this method up to 10 mL blood is placed in both anaerobic and aerobic Vital blood culture bottles. The bottles are then incubated in the Vital machine and continuously monitored for evidence of bacterial growth. When possible growth is identified, the bottle is removed from the incubator and a sample taken for Gram staining and subculture to agar plates. Over a period of 25 days an additional sample of 100 microliters for DNA extraction was taken from 116 unselected positive blood culture bottles, as described below. The DNA assay was performed without knowledge of the patient details or the initial Gram stain result.
Extraction of Bacterial DNA from Pure Bacterial Cultures.

Stored organisms were sub-cultured onto Columbia Blood Agar plates (Oxoid, UK). A single colony of overnight growth at 37° C. was suspended in 100 microliters of distilled water containing 1 microliter of a 1 mg/ml solution of lysostaphin (Sigma Chemical Co. UK) and incubated at 37° C. for 10 minutes. The tubes were then transferred to a thermo-cycler (Perkin-Elmer 2400 Gene amp PCR system) and heated to 95° C. for 10 minutes. Finally they were spun at 13,000 rpm for 2 minutes in a micro-centrifuge and 1 ml of the supernatant used in the 23S PCR described below.
Extraction of Bacterial DNA Directly from Vital Blood Culture Bottles.

DNA was extracted from all positive blood culture bottles in a Class II safety cabinet using the following protocol. Two to four drops of the broth were transferred into 0.5 ml of sterile distilled water at the time of aspiration for Gram stain and subculture. The tubes were spun at 13,000 rpm in a micro-centrifuge for 2 minutes and the supernatant discarded. The pellet was re-suspended in 100 microliters of distilled water containing 1 microliter of a 1 mg/ml solution of lysostaphin (Sigma, UK) and incubated at 37° C. for 20 minutes in a dry block (Scotlab, UK). The temperature was then raised to 95° C. and the tubes incubated for a further 15 minutes. Finally the tubes were spun at 13,000 rpm for 2 minutes in a micro-centrifuge and 1 microliter of the supernatant used in the 23S PCR described below.
Design of Primers to Amplify 23S Bacterial rDNA.
Forward primer ST23SP6
(SEQ ID NO: 1) 5' GCGATTTCYGAAYGGGGRAACCC
Reverse primer ST23SP10
(SEQ ID NO: 2) 5' digoxigenin-TTCGCCTTTCCCTCACG-GTACT Primers were commercially synthesized (Amersham Pharmacia, Amersham, UK). A PCR master mix containing 1× DnaZyme buffer (Flowgen, UK), 1 microMole Primer ST23SP6, 2 microMoles Primer SP23SP10, and 150 microMoles of each dNTP was made up in 5 ml quantities. Forty microliter aliquots of the master mix were dispensed into 100 microliter PCR tubes. When the DNA extracts were available 1 microliter of the appropriate extract and 1 unit of DnaZyme DNA polymerase (Flowgen, UK) added to each tube. The PCR mixes were then subjected to 5 cycles of 95° C. for 15 seconds, 55° C. for 15 seconds plus 72° C. for 15 seconds, followed by 25 cycles of 95° C. for 15 seconds plus 65° C. for 30 seconds. The presence of a PCR product was confirmed by agarose electrophoresis of 5 microliters and visualized with ethidium bromide.

Sequence Determination of Primary Pathogens and Identification of Potential Reverse Hybridization Targets.

Where species information was not available, we sequenced PCR products from selected isolates in our organism collection. This was supplemented by sequence data from products that failed to hybridize with the early oligonucleotide arrays or gave erroneous identifications. All the oligonucleotides chosen were targeted at sequences within a variable region of the PCR product. Using this sequence information, a panel of oligonucleotides with similar calculated melting temperatures was designed.

These sequences were tested in arrays using amplicons generated from reference organisms. Oligonucleotides not ideal as probes in the array due to low hybridization intensity were modified by the addition of low numbers of thymine bases (<20) to the 3' end of an oligonucleotide during synthesis. These modifications increase hybridization intensity. Thus by adjusting the number of thymine bases this technique was used to equalise the hybridisation intensity of the array.

Using this technique oligonucleotides with hybridization properties suitable for incorporation into the array were produced. This allows oligonucleotides that would have been unsuitable for inclusion in the array due to low intensity of hybridisation to be included in the same easily interpretable array.

Production of the Hybridization Membranes.

Figure 1:
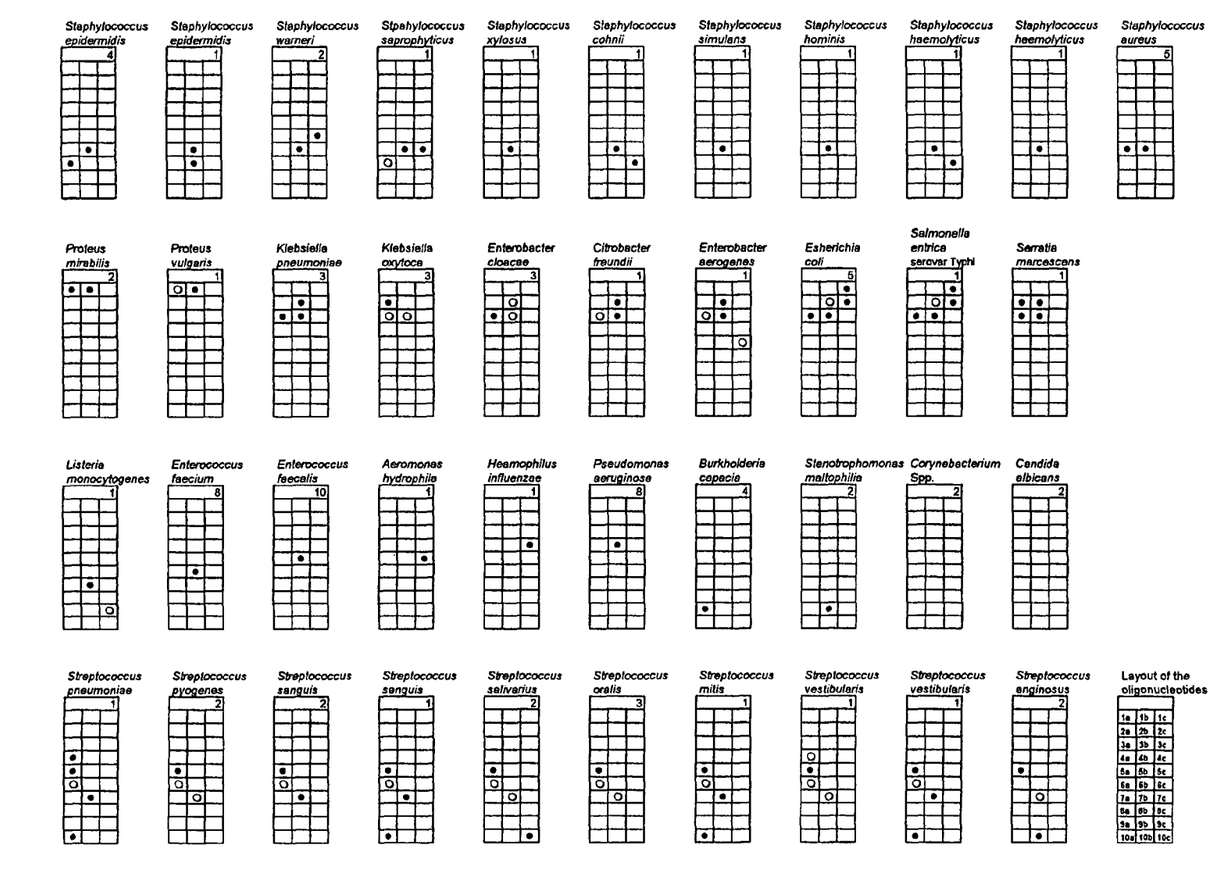
FIG. 1 shows one very convenient pattern of oligonucleotide probes fixed to a supporting strip.

One form of layout of target oligonucleotides is shown in FIG. 1. Oligonucleotides were synthesised and 50 pg of each in 0.3 microliters of water were spotted onto a specific position on a nylon membrane (MAGNA Micron Separations inc. MA, USA). A 3 mm grid was printed on the membrane with a bubble jet printer to allow the spots to be more accurately positioned. Strips were made in batches of 20. Once all the oligonucleotides had been applied the strips were dried and exposed to short wave UV in an Amplirad light box (Genetic Research Instruments, Essex, UK). The length of exposure was found to have a marked effect on the intensity of the resulting spots: with our UV illuminator 30 seconds was found to give the optimal spot intensity. After the oligonucleotides had been cross-linked to the membrane, any unbound oligonucleotides were removed by washing twice in 0.5×SSC plus 0.1% SDS for 2 minutes at 37° C. The strips were dried and stored at room temperature ready for use.

Hybridization Protocol.

The digoxigenin labeled 23S rDNA amplicons were hybridized to the oligonucleotide arrays using the following protocol. Each membrane was numbered and placed in a separate 2.5 ml screw-topped micro-centrifuge tube containing 0.5 ml of 5×SSC plus, 0.1% N-laurylsarcosine, 0.02% SDS, and 1% blocking reagent (Boehringer Mannheim, Germany). The digoxigenin PCR products were heated to 95° C. in a thermal cycler and the appropriate PCR product added directly to each tube. The hybridization was continued for 45 minutes at 50° C. with gentle agitation. The strips were then removed from the tubes washed four times in 25 ml 0.25×SSC plus 0.1% SDS, for each 20 strips, at 37° C. for 2 minutes. Any hybridization was detected using an anti-digoxigenin antibody conjugated to alkaline phosphatase amd detected colorimetrically (Boehringer Mannheim system). Color development was clearly visible between 15 minutes and 1 hour.

Assessment of the Primers.

The effectiveness of the primers was first assessed with DNA extracts from 79 stored bacterial isolates representing 28 species (Table 1). All the isolates tested produced products. A band of approximately 420 bp was produced with Gram positive bacteria and one of 390 bp for the Gram negative bacilli. Two isolates of *Candida albicans* were also processed using the same protocol but no PCR products were seen. No bands were seen in the DNA negative amplification controls.

Hybridizations from Enrichment Broths.

Over the course of the study samples from 408 culture positive Vitec bottles were subjected to PCR on the day they became positive.

The results obtained by the hybridization assay were compared to those subsequently obtained by conventional bacteriology (culture followed by phenotypic identification). Three hundred and fifty bottles (83.7%) produced correct identifications. These included nine (2.2%) in which mixed cultures were correctly identified. Mixtures identified included *Pseudomonas aeruginosa* plus *Enterococcus faecalis*, *Pseudomonas aeruginosa* plus *Stenotrophomonas maltophilia*, *Staphylococcus aureus* plus *Enterococcus faecalis*, CNS plus *Pseudomonas aeruginosa* and CNS plus *Enterococcus faecium*. Streptococcal DNA was identified in six bottles but no organisms subsequently grown, possibly indicating contamination of the enrichment bottles with streptococcal DNA. The remaining 43 (10.5%) bottles either contained no bacteria to which oligonucleotides were targeted or a PCR product was not obtained.

Assay Protocol

Solutions Needed (1) Polymerase Chain Reaction mixture:
Forward primer ST23SP6
Reverse primer ST23SP10

The PCR master mix was made up in 2.5 ml quantities containing all the ingredients for PCR except DNA polymerase. 12.5 microliter each primer 1 microgram/microliter (Pharmacia), 5 microliter each dNTP 100 mM (Pharmacia), 250 microliters 10× DnaZyme buffer (Flowgen, Staffordshire, UK), 2.2 ml water. This mixture should then be dispensed in 45 microliter aliquots into 200 microliter reaction tubes and 1 unit (0.5 microliter) of Taq polymerase (DnaZyme) added to the tubes just before they are required.

(2) Maleic acid buffer pH (7.5): 4.13 g sodium chloride and 5.53 g maleic acid in 500 ml of water, pH with 5 M NaOH (3) Detection buffer pH (9.5): 6.05 g tris-base and 2.97 g NaCl in 500 ml of water, pH with 10 N HCl (4) Blocking solution: 0.1 g Boehringer Mannheim blocking solution in 5 ml of detection buffer: make 2 hours before required.

(5) SSC: (20×) 3 M NaCl plus 0.3 M sodium citrate. Dilute to 0.25×SSC and keep at 37° C. ready for use.

(6) BCIP: 50 mg/ml 5-bromo-4-cloro-3-indolyl phosphate toluidinium salt in 100% dimethylformamide (7) NBT: 75 mg/ml nitroblue tetrazolium salt in 70% dimethylformamide Method This procedure will identify bacteria from positive Vitec blood culture bottles (Bio-Merioux, France). When aspirating the broth for Gram staining and sub-culture add 2 to 4 drops of the positive Vitec broth to one of the 2 ml screw-capped tubes containing 0.5 ml of sterile water and label the tube with the lab number.

DNA Extraction (to be Carried Out in the Containment Level 3 Laboratory)

(1) Spin the screw-capped tubes at high speed (10,000 g) for 4 minutes in a sealed rotor centrifuge.

(2) In a class 1 hood open the rotor and tubes and discard the Supernatant.

(3) Add 100 microliters of a 1 microgram/ml solution of lysostaphin (Sigma UK) made up in water.

(4) Place the tubes in a covered dry block and incubate at 37° C. for 20 minutes.

(5) Turn the dry block up to 95° C. and leave for 15 minutes.

The PCR and hybridization may now be carried out on the open bench in a laboratory.

Preparation of the Hybridization Strips

Strips were made either using the VP-scientific (San Diego, Calif., USA) multi print system which allows 96 spots to be simultaneously printed from a 384 well microtitre plate according to the manufactures instructions (replacing steps 1,2, and 3 below) or manually using the following procedure:

Manual Production of Hybridization Strips (1) Using a bubble jet printer print a grid of 20 strips onto a 18 cm by 3 cm section of nylon membrane (Magna nylon, MSI, Westboro Mass. or Nytran Supercharge, Schleicher and Schuell, Dassel GmbH, Germany).
(2) The vertical divisions between each strip should then be cut with a scalpel to avoid bleeding of the spots between strips.
(3) Approximately 0.3 microliters of each oligonucleotide (1 mg/ml solution in water) should then be spotted onto the appropriate position on each strip (see FIG. 1).
(4) Once dry, the membrane should be cross-linked by exposing to short wave UV in the Amplirad (GRI instruments UK) for 30 seconds.
(5) The membrane should then be washed 2 times in 50 ml of 0.5×SSC for 2 minutes and air dried.
(6) The membrane can now be stored dry at room temperature ready for use.

PCR Amplification

Add 1 microliter of the DNA extract to 45 microliters of the PCR mixture containing 0.5 microliters of DnyaZyme (Flowgen) in a 200 microliter PCR tube. A PCR negative control containing no bacterial DNA must be run alongside each set of PCR reactions.

In the PE thermal 2400 cycler (Perkin-Elmer Ltd.) carry out 5 cycles of 95° for 30 sec, 55° C. for 15 sec, 72° C. for 30 sec, followed by 25 cycles of 95° C. for 15 sec, 65° C. for 30 sec.

Hybridization (1) Heat the PCR reactions to 95° C. in the thermal cycler for 5 minutes.
(2) Label some hybridization strips and cut out with a scalpel and place in a screw-capped tube containing 0.5 ml of hybridization solution (5×SSC, 0.01% SDS, 0.01% N-laurylsarcosine, 1% blocking reagent (Boehringer Mannheim Germany)).
(3) Pipette the PCR reactions into the appropriate tubes.
(4) Hold the hybridization reactions at 50° C. for 45 minutes with gentle agitation.

Detection of Hybridization (1) Wash the strips 4 times in 25 ml of 0.25×SSC+0.1% SDS at 37° C. for 2 minutes.
(2) Flood the strips with 5 ml of blocking solution and leave for 15 minutes.
(3) Pour off the blocking solution and replace with 5 ml of maleic acid buffer containing 1 microliter of the Anti-digoxigenin antibody conjugate (Boehringer Mannheim, Germany). Leave for 10 minutes.
(4) Wash the strips 4 times in 25 ml of maleic acid buffer for 1 minute.
(5) Flood the strips with detection buffer.
(6) Prepare 5 ml of the detection solution by adding 45 microliters of BCIP and 35 microliters of NBT to 5 ml of detection buffer.
(7) Pour off the detection buffer from the strips and replace with the detection solution prepared above.
(8) Leave the strips in the dark for 15 minutes then examine them for detectable hybridization. Record the results, after 45 minutes and terminate the development by washing the strips in distilled water.

The method of the present invention can be used to identify bacteria in settings other than those described above, both clinical and non-clinical, also in non-medical, agricultural and environmental applications e.g. testing water supplies, and in pure cultures after isolation. The method overcomes the problems of other similar molecular diagnostic techniques described above. It allows rapid diagnosis of such organisms in blood or blood cultures or in other clinical specimens such as cerebrospinal fluid, urine, joint fluid, swab specimens, and abscesses. It provides a set of universal primers and experimental conditions that can be used to amplify potentially characteristic sequences of bacterial 23S rDNA. In particular, it provides a series of specific oligonucleotide targets that can be used simultaneously in a hybridization assay for the identification of clinically important bacteria.

TABLE 1

Strains used in this study and results of PCR amplifications and hybridizations from culture.

| Origin | Species | laboratory Code | Strong | Hybridization Weak |
|---|---|---|---|---|
| Blood culture STH | *Staphylococcus epidermidis* | 36839 | 27, 7b, 8a | |
| Blood culture STH | *Staphylococcus epidermidis* | 36938 | 27, 7b, 8a | |
| Blood culture STH | *Staphylococcus epidermidis* | 44.3 | 27, 7b, 8a | |
| Blood culture STH | *Staphylococcus epidermidis* | 37061 | 27, 7b, 8a | |
| Blood culture STH | *Staphylococcus epidermidis* | NCTC11047 | 27, 7b | |
| Blood culture STH | *Staphylococcus warneri* | B5 | 27, 7b | |
| Blood culture STH | *Staphylococcus saprophyticus* | B6 | 27, 7b | 8a |
| Blood culture STH | *Staphylococcus xylosus* | B7 | 27, 7b | |
| Blood culture STH | *Staphylococcus cohnii* | B8 | 27, 7b | |
| Blood culture STH | *Staphylococcus simulans* | B9 | 27, 7b | |
| Blood culture STH | *Staphylococcus hominis* | B10 | 27, 7b | |
| Blood culture STH | *Staphylococcus haemolyticus* | B11 | 27, 7b | |
| Blood culture STH | *Staphylococcus haemolyticus* | 31871 | 27, 7b | |
| NCTC | *Staphylococcus aureus* | NCTC6571 | 27, 7b 7a | |
| GH | *Staphylococcus aureus* (MR) | GH25 | 27, 7b 7a | |
| GH | *Staphylococcus aureus* (MR) | GH7 | 27, 7b 7a | |
| Blood culture STH | *Staphylococcus aureus* (MR) | 816.98 | 27, 7b 7a | |
| Blood culture STH | *Staphylococcus aureus* (MS) | 36989 | 27, 7b 7a | |
| Blood culture STH | *Streptococcus milleri* | 676.98 | 27 | |
| Blood culture STH | *Streptococcus milleri* | 662.98 | 27 | |
| Blood culture STH | *Streptococcus pneumoniae* | 697.98 | 27, 5a | 5b 7b 6a |

TABLE 1-continued

Strains used in this study and results of PCR amplifications and hybridizations from culture.

| Origin | Species | laboratory Code | Strong | Hybridization Weak |
|---|---|---|---|---|
| Blood culture STH | *Streptococcus pneumoniae* | 76a.98 | 27, 5a | 7b |
| Blood culture STH | *Streptococcus pneumoniae* | 736.98 | 27, 5a | 7b |
| Blood culture STH | *Streptococcus* spp. (viridans) | 738.98 | 27, 5a | 7b |
| Blood culture STH | *Streptococcus* GroupG | 776.98 | 27, 5a | |
| feces (VRE) | *Enterococcus faecium* | 147 | 27, 6b | |
| feces (VRE) | *Enterococcus faecium* | 152 | 27, 6b | |
| feces STH | *Enterococcus faecium* | 7 | 27, 6b | |
| feces STH | *Enterococcus faecium* | 24 | 27, 6b | |
| feces STH | *Enterococcus faecium* | 39 | 27, 6b | |
| feces STH | *Enterococcus faecium* | 40 | 27, 6b | |
| Blood culture STH | *Enterococcus faecium* | 848.98 | 27, 6b | |
| Blood culture STH | *Enterococcus faecium* | 665.98 | 27, 6b | |
| feces STH | *Enterococcus faecalis* | 20 | 27, 5b | |
| feces STH | *Enterococcus faecalis* | 23 | 27, 5b | |
| feces STH | *Enterococcus faecalis* | 24 | 27, 5b | |
| feces STH | *Enterococcus faecalis* | 25 | 27, 5b | |
| feces STH | *Enterococcus faecalis* | 27 | 27, 5b | |
| feces STH | *Enterococcus faecalis* | 82 | 27, 5b | |
| Blood culture STH | *Enterococcus faecalis* | 707.98 | 27, 5b | |
| Blood culture STH | *Enterococcus faecalis* | 706.98 | 27, 5b | |
| Blood culture STH | *Enterococcus faecalis* | 708.98 | 27, 5b | |
| Blood culture STH | *Enterococcus faecalis* | 835.98 | 27, 5b | |
| NCTC | *Escherichia coli* | NCTC8879 | 27, 3b | 3a, 2b |
| Blood culture STH | *Escherichia coli* | 817.98 | 27, 3b | 3a, 2b |
| Blood culture STH | *Escherichia coli* | 794.98 | 27, 3b | 3a, 2b |
| Blood culture STH | *Escherichia coli* | 829.98 | 27, 3b | 3a, 2b |
| Blood culture STH | *Escherichia coli* | 780.98 | 27, 3b | 3a, 2b |
| Blood culture STH | *Klebsiella oxytoca* | 800.98 | 27, 2a | 3a, 2b |
| Blood culture STH | *Klebsiella oxytoca* | 243a.95 | 27, 2a | 3a, 2b |
| Blood culture STH | *Klebsiella oxytoca* | 97.92 | 27, 2a | 3a, 2b |
| Blood culture STH | *Klebsiella pneumoniae* | 767.98 | 27, 2b | 3a, 2b |
| Blood culture STH | *Klebsiella pneumoniae* | 851.98 | 27, 2b | 3a, 3b |
| Blood culture STH | *Klebsiella pneumoniae* | 842.98 | 27, 2b | 3a, 3b |
| Blood culture STH | *Enterobacter cloacae* | 770.98 | 27, 3a | 2b, 3b |
| Blood culture STH | *Enterobacter cloacae* | 814.98 | 27, 3a | 2b, 3b |
| Blood culture STH | *Enterobacter cloacae* | 810.98 | 27, 3a | 2b, 3b |
| Blood culture STH | *Enterobacter aerogenes* | 743.98 | 27, 2b | 3a, 3b |
| 382010 | *Citrobacter freundii* | 382010 | 27, 2b, 3b | 3a |
| Blood culture STH | *Proteus mirabilis* | 827.98 | 27, 1a, 1b | |
| Blood culture STH | *Proteus mirabilis* | 838.98 | 27, 1a, 1b | |
| Blood culture STH | *Proteus mirabilis* | 703.98 | 27, 1a, 1b | |
| Blood culture STH | *Serratia marcesens* | 1087.98 | 27, 2a, 2b, 3a, 3b | |
| Blood culture STH | *Pseudomonas aeruginosa* | 37036 | 27, 4b | |
| Blood culture STH | *Pseudomonas aeruginosa* | 812.98 | 27, 4b | |
| Blood culture STH | *Pseudomonas aeruginosa* | 728.98 | 27, 4b | |
| Blood culture STH | *Pseudomonas aeruginosa* | 714.98 | 27, 4b | |
| Blood culture STH | *Pseudomonas aeruginosa* | 760.98 | 27, 4b | |
| Blood culture STH | *Pseudomonas aeruginosa* | 702.98 | 27, 4b | |
| Blood culture STH | *Pseudomonas aeruginosa* | 845.98 | 27, 4b | |
| Blood culture STH | *Pseudomonas aeruginosa* | 37036 | 27, 4b | |
| Blood culture STH | *Stenotrophomonas maltophilia* | 822.98 | 27, 4b | |
| Blood culture STH | *Stenotrophomonas maltophilia* | 824.98 | 27, 4b | |
| CF patient LH | *Burkholderia cepacia* | H7 | 27, 4b | |
| CF patient LH | *Burkholderia cepacia* | F3 | 27, 4b | |
| CF patient LH | *Burkholderia cepacia* | TR1 | 27, 4b | |
| CF patient LH | *Burkholderia cepacia* | H9 | 27, 4b | |
| Blood culture STH | Coryneform | Co1 | No Hybridization | |
| Blood culture STH | Coryneform | Co2 | No Hybridization | |
| Blood culture STH | *Candida albicans* | C1 | No amplicon or Hybridization | |
| Blood culture STH | *Candida albicans* | C2 | No amplicon or Hybridization | |

TABLE 1. Footnote
STH = St. Thomas' Hospital, GH = Guy's Hospital, LH = Lewisham Hospital, CF = Cystic fibrosis. NCTC = National Collection of Type Cultures, VRE = vancomycin resistant *enterococci*. MR = methicillin resistant, MS = methicillin sensitive

Sequence Listings for the primers and oligonucleotides used for the purposes of the present invention are given below.

A method for identifying bacteria in a sample is described which comprises amplifying a portion of the 23S rDNA present in the sample using a degenerate primer set comprising one or more DNA molecules consisting essentially of DNA having the sequence(s) 5'GCGATTTCYGA-AYGGGGRAACCC (SEQ ID NO: 1), and 5'TTCGC-CTTTCCCTCACGGTACT (SEQ ID NO: 2) and testing the resulting amplicon by hybridisation to one or more oligonucleotide probes designed to identify one or more bacteria likely to be present in the sample. The method allows for the identification of a variety of bacteria in a single test including *Escherichia coli, Staphylococcus aureus, Pseudomonas aeruginosa, Enterococcus* spp., *Klebsiella* spp., *Enterobacter* spp., *Proteus* spp., *Pneumococci*, and coagulase-negative *Staphylococci*. One or more novel oligonucleotides for use in this test are immobilised on a solid carrier and incorporated in a diagnostic test kit for use in hospitals and other environments.

The invention claimed is:

1. A method for identifying one or more bacteria in a test sample, the method comprising:
   (a) amplifying a portion of 23S rDNA present in the test sample by polymerase chain reaction (PCR) or transcription mediated amplification using a first primer consisting of SEQ ID NO: 1 and a second primer consisting of SEQ ID NO: 2, to thereby yield amplicons; and then
   (b) probing with the amplicons of step (a) oligonucleotides designed to identify bacteria which may be present in the sample, wherein selective hybridization of the amplicons to the oligonucleotides indicates the identity of the bacteria present in the sample, and wherein the oligonucleotides have sequences selected from the group consisting of SEQ ID NOs: 3, 4, 6-7, 9-13, 15-19, 22-28, 30, 37-39, 42-47, 49, and 51-56.

2. The method according to claim 1, wherein in step (b) oligonucleotides designed to identify at least eight bacterial species are probed.

3. The method according to claim 1, in which are probed oligonucleotides designed to designed to identify at least one of *Listeria* spp., *Stenotrophomonas maltophilia*, *Burkholderia cepacia*, *Escherichia coli*, *Staphylococcus aureus*, *Pseudomonas aeruginosa*, *Enterococcus* spp., *Klebsiella* spp., *Enterobacter* spp., *Proteus mirabilis*, *Pneumococci*, and coagulase-negative *Staphylococci*.

4. The method according to claim 1, wherein in step (b) oligonucleotides designed to identify at least ten bacterial species are probed.

5. The method according to claim 1, in which the oligonucleotides are attached to a support material.

* * * * *

```
                           SEQUENCE LISTING

<160> NUMBER OF SEQ ID NOS: 61

<210> SEQ ID NO 1
<211> LENGTH: 23
<212> TYPE: DNA
<213> ORGANISM: Artificial Sequence
<220> FEATURE:
<223> OTHER INFORMATION: PCR Primer

<400> SEQUENCE: 1
gcgatttcyg aaygggggraa ccc                                          23

<210> SEQ ID NO 2
<211> LENGTH: 22
<212> TYPE: DNA
<213> ORGANISM: Artificial Sequence
<220> FEATURE:
<223> OTHER INFORMATION: PCR Primer

<400> SEQUENCE: 2
ttcgcctttc cctcacggta ct                                            22

<210> SEQ ID NO 3
<211> LENGTH: 25
<212> TYPE: DNA
<213> ORGANISM: Artificial Sequence
<220> FEATURE:
<223> OTHER INFORMATION: PCR Primer

<400> SEQUENCE: 3
aatagcagtg tcaggagaac ggtct                                         25

<210> SEQ ID NO 4
<211> LENGTH: 23
<212> TYPE: DNA
<213> ORGANISM: Artificial Sequence
<220> FEATURE:
<223> OTHER INFORMATION: PCR Primer

<400> SEQUENCE: 4
atagccccgt atctgaagat gct                                           23

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
ccagagcctg aatcagtgtg t                                             21

<210> SEQ ID NO 6
<211> LENGTH: 23
<212> TYPE: DNA
<213> ORGANISM: Artificial Sequence
<220> FEATURE:
<223> OTHER INFORMATION: PCR Primer

<400> SEQUENCE: 6
tcccgtacac taaaacgcac agg                                           23
```

```
<210> SEQ ID NO 7
<211> LENGTH: 23
<212> TYPE: DNA
<213> ORGANISM: Artificial Sequence
<220> FEATURE:
<223> OTHER INFORMATION: PCR Primer

<400> SEQUENCE: 7
tcccgtacac caaaatgcac agg                                          23

<210> SEQ ID NO 8
<211> LENGTH: 21
<212> TYPE: DNA
<213> ORGANISM: Artificial Sequence
<220> FEATURE:
<223> OTHER INFORMATION: PCR Primer

<400> SEQUENCE: 8
cagagcctga atcagtatgt g                                            21

<210> SEQ ID NO 9
<211> LENGTH: 23
<212> TYPE: DNA
<213> ORGANISM: Artificial Sequence
<220> FEATURE:
<223> OTHER INFORMATION: PCR Primer

<400> SEQUENCE: 9
tcccgtacac gaaaatgcac agg                                          23

<210> SEQ ID NO 10
<211> LENGTH: 20
<212> TYPE: DNA
<213> ORGANISM: Artificial Sequence
<220> FEATURE:
<223> OTHER INFORMATION: PCR Primer

<400> SEQUENCE: 10
cccgtacaca aaaatgcaca                                              20

<210> SEQ ID NO 11
<211> LENGTH: 21
<212> TYPE: DNA
<213> ORGANISM: Artificial Sequence
<220> FEATURE:
<223> OTHER INFORMATION: PCR Primer

<400> SEQUENCE: 11
agagcctgaa tcagcatgtg t                                            21

<210> SEQ ID NO 12
<211> LENGTH: 22
<212> TYPE: DNA
<213> ORGANISM: Artificial Sequence
<220> FEATURE:
<223> OTHER INFORMATION: PCR Primer

<400> SEQUENCE: 12
agaagaatga tttgggaaga tc                                           22

<210> SEQ ID NO 13
<211> LENGTH: 22
<212> TYPE: DNA
<213> ORGANISM: Artificial Sequence
<220> FEATURE:
```

<223> OTHER INFORMATION: PCR Primer

<400> SEQUENCE: 13
gcttcattga ttttagcgga ac                                          22

<210> SEQ ID NO 14
<211> LENGTH: 22
<212> TYPE: DNA
<213> ORGANISM: Artificial Sequence
<220> FEATURE:
<223> OTHER INFORMATION: PCR Primer

<400> SEQUENCE: 14
gtgaggagaa tgtgttggga ag                                          22

<210> SEQ ID NO 15
<211> LENGTH: 21
<212> TYPE: DNA
<213> ORGANISM: Artificial Sequence
<220> FEATURE:
<223> OTHER INFORMATION: PCR Primer

<400> SEQUENCE: 15
agaagaagac ctgggaaag g                                            21

<210> SEQ ID NO 16
<211> LENGTH: 24
<212> TYPE: DNA
<213> ORGANISM: Artificial Sequence
<220> FEATURE:
<223> OTHER INFORMATION: PCR Primer

<400> SEQUENCE: 16
ggtagtctgt tagtatagtt gaag                                        24

<210> SEQ ID NO 17
<211> LENGTH: 20
<212> TYPE: DNA
<213> ORGANISM: Artificial Sequence
<220> FEATURE:
<223> OTHER INFORMATION: PCR Primer

<400> SEQUENCE: 17
tggaacggtc ctggaaaggc                                             20

<210> SEQ ID NO 18
<211> LENGTH: 20
<212> TYPE: DNA
<213> ORGANISM: Artificial Sequence
<220> FEATURE:
<223> OTHER INFORMATION: PCR Primer

<400> SEQUENCE: 18
agaagaacta cctggaaggt                                             20

<210> SEQ ID NO 19
<211> LENGTH: 22
<212> TYPE: DNA
<213> ORGANISM: Artificial Sequence
<220> FEATURE:
<223> OTHER INFORMATION: PCR Primer

<400> SEQUENCE: 19
ggtagttctt tcagatagtc gg                                          22

```
<210> SEQ ID NO 20
<211> LENGTH: 30
<212> TYPE: DNA
<213> ORGANISM: Artificial Sequence
<220> FEATURE:
<223> OTHER INFORMATION: PCR Primer

<400> SEQUENCE: 20
acggagttac aaaagtatat attagttttt                                      30

<210> SEQ ID NO 21
<211> LENGTH: 24
<212> TYPE: DNA
<213> ORGANISM: Artificial Sequence
<220> FEATURE:
<223> OTHER INFORMATION: PCR Primer

<400> SEQUENCE: 21
acggagttac aaaggacgac atta                                            24

<210> SEQ ID NO 22
<211> LENGTH: 26
<212> TYPE: DNA
<213> ORGANISM: Artificial Sequence
<220> FEATURE:
<223> OTHER INFORMATION: PCR Primer

<400> SEQUENCE: 22
ggttgtagga cactctatac ggagtt                                          26

<210> SEQ ID NO 23
<211> LENGTH: 30
<212> TYPE: DNA
<213> ORGANISM: Artificial Sequence
<220> FEATURE:
<223> OTHER INFORMATION: PCR Primer

<400> SEQUENCE: 23
acggagttac aaaagaacag actagttttt                                      30

<210> SEQ ID NO 24
<211> LENGTH: 25
<212> TYPE: DNA
<213> ORGANISM: Artificial Sequence
<220> FEATURE:
<223> OTHER INFORMATION: PCR Primer

<400> SEQUENCE: 24
acggagttac aaaagaacat gttag                                           25

<210> SEQ ID NO 25
<211> LENGTH: 25
<212> TYPE: DNA
<213> ORGANISM: Artificial Sequence
<220> FEATURE:
<223> OTHER INFORMATION: PCR Primer

<400> SEQUENCE: 25
atggagttac aaaagaatcg attag                                           25

<210> SEQ ID NO 26
<211> LENGTH: 30
<212> TYPE: DNA
<213> ORGANISM: Artificial Sequence
<220> FEATURE:
<223> OTHER INFORMATION: PCR Primer
```

<400> SEQUENCE: 26
acggagttac aaaggaatat attagttttt                                30

<210> SEQ ID NO 27
<211> LENGTH: 22
<212> TYPE: DNA
<213> ORGANISM: Artificial Sequence
<220> FEATURE:
<223> OTHER INFORMATION: PCR Primer

<400> SEQUENCE: 27
cgtattgtta gccgaacgct ct                                        22

<210> SEQ ID NO 28
<211> LENGTH: 22
<212> TYPE: DNA
<213> ORGANISM: Artificial Sequence
<220> FEATURE:
<223> OTHER INFORMATION: PCR Primer

<400> SEQUENCE: 28
agccctgtat ctgaaagggc ca                                        22

<210> SEQ ID NO 29
<211> LENGTH: 30
<212> TYPE: DNA
<213> ORGANISM: Artificial Sequence
<220> FEATURE:
<223> OTHER INFORMATION: PCR Primer

<400> SEQUENCE: 29
acggagttac aaagaaagt tataattttt                                30

<210> SEQ ID NO 30
<211> LENGTH: 21
<212> TYPE: DNA
<213> ORGANISM: Artificial Sequence
<220> FEATURE:
<223> OTHER INFORMATION: PCR Primer

<400> SEQUENCE: 30
agaagaacta cctgggaagg t                                         21

<210> SEQ ID NO 31
<211> LENGTH: 27
<212> TYPE: DNA
<213> ORGANISM: Artificial Sequence
<220> FEATURE:
<223> OTHER INFORMATION: PCR Primer

<400> SEQUENCE: 31
acggcagaag ggcaaaccga atttttt                                   27

<210> SEQ ID NO 32
<211> LENGTH: 27
<212> TYPE: DNA
<213> ORGANISM: Artificial Sequence
<220> FEATURE:
<223> OTHER INFORMATION: PCR Primer

<400> SEQUENCE: 32
ggcaggaggg caaaccgaag attttt                                    27

<210> SEQ ID NO 33
<211> LENGTH: 27

```
<212> TYPE: DNA
<213> ORGANISM: Artificial Sequence
<220> FEATURE:
<223> OTHER INFORMATION: PCR Primer

<400> SEQUENCE: 33
ggcaagaggg caaaccgaag atttttt                                              27

<210> SEQ ID NO 34
<211> LENGTH: 24
<212> TYPE: DNA
<213> ORGANISM: Artificial Sequence
<220> FEATURE:
<223> OTHER INFORMATION: PCR Primer

<400> SEQUENCE: 34
cgctctggga agtgcgaacg tttt                                                 24

<210> SEQ ID NO 35
<211> LENGTH: 24
<212> TYPE: DNA
<213> ORGANISM: Artificial Sequence
<220> FEATURE:
<223> OTHER INFORMATION: PCR Primer

<400> SEQUENCE: 35
gaaaggcgcg cgatacaggg tttt                                                 24

<210> SEQ ID NO 36
<211> LENGTH: 24
<212> TYPE: DNA
<213> ORGANISM: Artificial Sequence
<220> FEATURE:
<223> OTHER INFORMATION: PCR Primer

<400> SEQUENCE: 36
gaaagtccga cggtacaggg tttt                                                 24

<210> SEQ ID NO 37
<211> LENGTH: 30
<212> TYPE: DNA
<213> ORGANISM: Artificial Sequence
<220> FEATURE:
<223> OTHER INFORMATION: PCR Primer

<400> SEQUENCE: 37
acggagttac aaaagaacat gttagttttt                                           30

<210> SEQ ID NO 38
<211> LENGTH: 30
<212> TYPE: DNA
<213> ORGANISM: Artificial Sequence
<220> FEATURE:
<223> OTHER INFORMATION: PCR Primer

<400> SEQUENCE: 38
acggagttac aaaagaattt gttagttttt                                           30

<210> SEQ ID NO 39
<211> LENGTH: 20
<212> TYPE: DNA
<213> ORGANISM: Artificial Sequence
<220> FEATURE:
<223> OTHER INFORMATION: PCR Primer

<400> SEQUENCE: 39
```

```
gttagtggaa cggattggaa                                              20

<210> SEQ ID NO 40
<211> LENGTH: 24
<212> TYPE: DNA
<213> ORGANISM: Artificial Sequence
<220> FEATURE:
<223> OTHER INFORMATION: PCR Primer

<400> SEQUENCE: 40
tgaccatagc gggtgacagt cttt                                         24

<210> SEQ ID NO 41
<211> LENGTH: 24
<212> TYPE: DNA
<213> ORGANISM: Artificial Sequence
<220> FEATURE:
<223> OTHER INFORMATION: PCR Primer

<400> SEQUENCE: 41
tgaccatagt gggtgacagt cttt                                         24

<210> SEQ ID NO 42
<211> LENGTH: 22
<212> TYPE: DNA
<213> ORGANISM: Artificial Sequence
<220> FEATURE:
<223> OTHER INFORMATION: PCR Primer

<400> SEQUENCE: 42
gtgagtttag cagaacattc tg                                           22

<210> SEQ ID NO 43
<211> LENGTH: 24
<212> TYPE: DNA
<213> ORGANISM: Artificial Sequence
<220> FEATURE:
<223> OTHER INFORMATION: PCR Primer

<400> SEQUENCE: 43
taagtaaggt tagtagaaca ctct                                         24

<210> SEQ ID NO 44
<211> LENGTH: 22
<212> TYPE: DNA
<213> ORGANISM: Artificial Sequence
<220> FEATURE:
<223> OTHER INFORMATION: PCR Primer

<400> SEQUENCE: 44
catccaagag aacgctttag ca                                           22

<210> SEQ ID NO 45
<211> LENGTH: 22
<212> TYPE: DNA
<213> ORGANISM: Artificial Sequence
<220> FEATURE:
<223> OTHER INFORMATION: PCR Primer

<400> SEQUENCE: 45
aatgggatca gccttgtact ct                                           22

<210> SEQ ID NO 46
<211> LENGTH: 21
<212> TYPE: DNA
<213> ORGANISM: Artificial Sequence
```

<220> FEATURE:
<223> OTHER INFORMATION: PCR Primer

<400> SEQUENCE: 46
tctggaaagg cgcgcgatac a                                              21

<210> SEQ ID NO 47
<211> LENGTH: 21
<212> TYPE: DNA
<213> ORGANISM: Artificial Sequence
<220> FEATURE:
<223> OTHER INFORMATION: PCR Primer

<400> SEQUENCE: 47
gtctggaaag tccgacggta c                                              21

<210> SEQ ID NO 48
<211> LENGTH: 25
<212> TYPE: DNA
<213> ORGANISM: Artificial Sequence
<220> FEATURE:
<223> OTHER INFORMATION: PCR Primer

<400> SEQUENCE: 48
accatatttt taatatgggg ttttt                                          25

<210> SEQ ID NO 49
<211> LENGTH: 19
<212> TYPE: DNA
<213> ORGANISM: Artificial Sequence
<220> FEATURE:
<223> OTHER INFORMATION: PCR Primer

<400> SEQUENCE: 49
ccacattttt aatgtgggg                                                 19

<210> SEQ ID NO 50
<211> LENGTH: 23
<212> TYPE: DNA
<213> ORGANISM: Artificial Sequence
<220> FEATURE:
<223> OTHER INFORMATION: PCR Primer

<400> SEQUENCE: 50
ccgagctgaa gaagcgaggg ttt                                            23

<210> SEQ ID NO 51
<211> LENGTH: 24
<212> TYPE: DNA
<213> ORGANISM: Artificial Sequence
<220> FEATURE:
<223> OTHER INFORMATION: PCR Primer

<400> SEQUENCE: 51
cctttcgagg ttatgtatac tgaa                                           24

<210> SEQ ID NO 52
<211> LENGTH: 21
<212> TYPE: DNA
<213> ORGANISM: Artificial Sequence
<220> FEATURE:
<223> OTHER INFORMATION: PCR Primer

<400> SEQUENCE: 52
ggtgttgcat tcgtggggtt g                                              21

<210> SEQ ID NO 53
<211> LENGTH: 20
<212> TYPE: DNA
<213> ORGANISM: Artificial Sequence
<220> FEATURE:
<223> OTHER INFORMATION: PCR Primer

<400> SEQUENCE: 53
gggttgcgta tggagggttg                                                     20

<210> SEQ ID NO 54
<211> LENGTH: 19
<212> TYPE: DNA
<213> ORGANISM: Artificial Sequence
<220> FEATURE:
<223> OTHER INFORMATION: PCR Primer

<400> SEQUENCE: 54
gcgctacccg gctgagagg                                                      19

<210> SEQ ID NO 55
<211> LENGTH: 21
<212> TYPE: DNA
<213> ORGANISM: Artificial Sequence
<220> FEATURE:
<223> OTHER INFORMATION: PCR Primer

<400> SEQUENCE: 55
ctacctggct gaggggtagt c                                                   21

<210> SEQ ID NO 56
<211> LENGTH: 21
<212> TYPE: DNA
<213> ORGANISM: Artificial Sequence
<220> FEATURE:
<223> OTHER INFORMATION: PCR Primer

<400> SEQUENCE: 56
ggacgatacg tctcagctct a                                                   21

<210> SEQ ID NO 57
<211> LENGTH: 24
<212> TYPE: DNA
<213> ORGANISM: Artificial Sequence
<220> FEATURE:
<223> OTHER INFORMATION: PCR Primer

<400> SEQUENCE: 57
tgactgaccg atagygaacc agta                                                24

<210> SEQ ID NO 58
<211> LENGTH: 21
<212> TYPE: DNA
<213> ORGANISM: Artificial Sequence
<220> FEATURE:
<223> OTHER INFORMATION: PCR Primer

<400> SEQUENCE: 58
tgaccatagc gggtgacagt c                                                   21

<210> SEQ ID NO 59
<211> LENGTH: 21
<212> TYPE: DNA
<213> ORGANISM: Artificial Sequence
<220> FEATURE:
<223> OTHER INFORMATION: PCR Primer

```
<400> SEQUENCE: 59
tgaccatagt gggtgacagt c                                            21

<210> SEQ ID NO 60
<211> LENGTH: 20
<212> TYPE: DNA
<213> ORGANISM: Artificial Sequence
<220> FEATURE:
<223> OTHER INFORMATION: PCR Primer

<400> SEQUENCE: 60
accatatttt taatatgggg                                              20

<210> SEQ ID NO 61
<211> LENGTH: 20
<212> TYPE: DNA
<213> ORGANISM: Artificial Sequence
<220> FEATURE:
<223> OTHER INFORMATION: PCR Primer

<400> SEQUENCE: 61
ccgagctgaa gaagcgaggg                                              20
```